(12) United States Patent
Nouri

(10) Patent No.: US 9,572,644 B2
(45) Date of Patent: Feb. 21, 2017

(54) TRAY

(76) Inventor: Mohammad Reza Nouri, Vancouver (CA)

(*) Notice: Subject to any disclaimer, the term of this patent is extended or adjusted under 35 U.S.C. 154(b) by 284 days.

(21) Appl. No.: 14/000,399

(22) PCT Filed: Feb. 20, 2012

(86) PCT No.: PCT/CA2012/050100
§ 371 (c)(1),
(2), (4) Date: Aug. 20, 2013

(87) PCT Pub. No.: WO2012/109762
PCT Pub. Date: Aug. 23, 2012

(65) Prior Publication Data
US 2013/0327658 A1    Dec. 12, 2013

Related U.S. Application Data

(60) Provisional application No. 61/444,785, filed on Feb. 20, 2011.

(51) Int. Cl.
*A61C 19/02* (2006.01)
*A61C 19/00* (2006.01)

(52) U.S. Cl.
CPC ............. *A61C 19/02* (2013.01); *A61B 90/92* (2016.02); *A61C 19/005* (2013.01); *A61B 50/20* (2016.02); *A61B 50/33* (2016.02); *A61B 2050/0059* (2016.02)

(58) Field of Classification Search
CPC ... A61C 19/02; A61C 19/005; A61C 2202/00; A61C 8/0087; B65D 85/00; A61B 19/026

USPC ....... 206/63.5, 368, 461; 220/23.83; 433/50, 433/53, 49, 163
See application file for complete search history.

(56) References Cited

U.S. PATENT DOCUMENTS

| | | | |
|---|---|---|---|
| 2,970,379 A | 2/1961 | Hardgrove et al. | |
| 3,697,223 A | 10/1972 | Kovalcik et al. | |
| 3,966,094 A | 6/1976 | Sheppard | |
| 4,901,850 A * | 2/1990 | McIntosh | B44D 3/02 206/1.7 |
| 4,991,759 A | 2/1991 | Scharf | |
| 5,139,188 A | 8/1992 | Scharf | |
| 5,226,536 A * | 7/1993 | Elliott | 206/369 |
| 5,249,963 A | 10/1993 | McGarrigle | |
| 5,325,958 A * | 7/1994 | Arasim | B44D 3/04 206/1.7 |
| 5,327,838 A * | 7/1994 | Beltman | 108/25 |
| 5,377,823 A * | 1/1995 | Steen et al. | 206/63.5 |
| 5,529,493 A | 6/1996 | Rafetto, Jr. | |

(Continued)

FOREIGN PATENT DOCUMENTS

| | | |
|---|---|---|
| DE | 19930466 A1 | 1/2001 |
| DE | 20314104 U1 | 11/2003 |
| WO | WO9607364 A1 | 3/1996 |

*Primary Examiner* — Steven A. Reynolds
(74) *Attorney, Agent, or Firm* — Clark Wilson LLP

(57) ABSTRACT

The present invention relates apparatus for holding material to be dispensed in a surgical setting, and in particular that: (a) allows for small portions of material to be dispensed efficiently, (b) resists evaporation of volatile agents in the material being dispensed, (c) reduces exposure of the material to light and actinic radiation during intermittent use, and (d) supports autoclaving in order to fulfill sterilization standards in surgical setting.

21 Claims, 10 Drawing Sheets

(56) References Cited

U.S. PATENT DOCUMENTS

| | | | |
|---|---|---|---|
| 5,749,730 A | | 5/1998 | Johnsen et al. |
| 5,947,278 A | * | 9/1999 | Sawhney et al. ............. 206/216 |
| 6,220,458 B1 | * | 4/2001 | Falor .............................. 211/74 |
| 7,090,073 B2 | | 8/2006 | Barnes |
| 2006/0226032 A1 | * | 10/2006 | Zalsman ....................... 206/63.5 |
| 2008/0156667 A1 | * | 7/2008 | Huggins .................. B44D 3/04 |
| | | | 206/1.8 |
| 2008/0230415 A1 | | 9/2008 | Mark |
| 2009/0188815 A1 | | 7/2009 | Ahlers |
| 2013/0327658 A1 | * | 12/2013 | Nouri .......................... 206/63.5 |

* cited by examiner

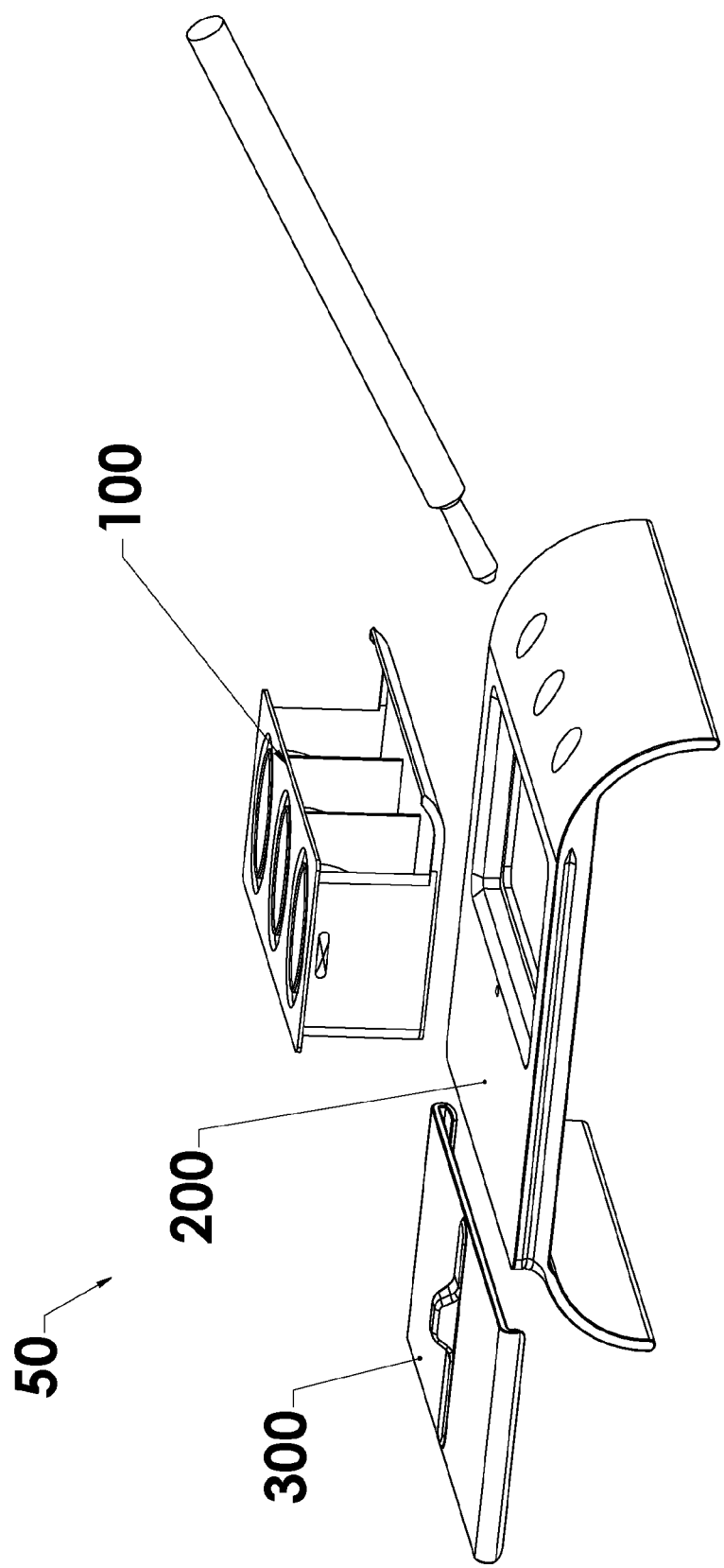

TRAY

CROSS REFERENCE TO RELATED APPLICATIONS

This application claims priority from U.S. Provisional Patent Application Ser. No. 61/444,785 filed on Feb. 20, 2011, entitled AUTOCLAVABLE DISPENSING TRAY, which is expressly incorporated by reference herein.

BACKGROUND OF THE INVENTION

1. Field of the Invention

The present invention relates to trays for dispensing materials that are volatile and sensitive to setting by exposure to visible light or actinic radiation. The invention has particular application, for example, in the field of dentistry; however, the invention may also be used in other applications, including medical and surgical applications.

2. Description of Related Art

Photocurable resin composite materials, and related conditioning and bonding materials, are increasingly being used in dental and surgical settings. These materials are often sensitive to premature evaporation or setting by light or actinic radiation.

Therefore, effective use of such materials demands a dispensing apparatus that:
  allows for small portions of material to be dispensed efficiently,
  resists evaporation of volatile agents in the material being dispensed, and
  reduces exposure of the material to light and actinic radiation during intermittent use.

When used for dental and surgical applications, in particular, a fully sterile environment is important. Therefore, it is important that any such dispensing apparatus be comprised of parts that can be made sterile, for example through radiation or autoclaving, either for single or multiple usages, and in the case of single usage, conveniently replaced, all to fulfill infection control standards.

Conventional dispensing apparatus suffer from a number of disadvantages. They typically hold material in shallow, wide-mouthed wells that expose a large proportion of the material to the environment for evaporation and radiation, risking premature setting of the exposed proportion, such wells being typically shaped as shallow square prisms or shallow cylinders or shallow segments of spheres.

Covers to protect the wells are often difficult to operate, so that users will not cover the wells during short intervals between uses. Wells are prone to spill material, for example into adjacent wells, causing cross-contamination. And conventional dispensing apparatus are often difficult to sterilize because of the materials from which they are made and/or because they are shaped with crannies that trap and hold contaminants. Furthermore, conventional dispensing apparatus don't hold dispensing tools for ready access while safe from cross-contamination.

Accordingly, what is needed is a better way to sterilely dispense compounds that can prematurely set through evaporation or radiation.

SUMMARY OF THE INVENTION

The present invention is directed to this need.

According to one aspect of the present invention, there is provided an apparatus for holding material to be dispensed, comprising: a well having a cavity for holding the material, the cavity having a cavity depth, a cavity length, a cavity width and a cavity cross-sectional area, and a passage in communication with the cavity, such that material can be placed into the cavity and removed from the cavity through the passage, the passage having a passage depth, a passage length, a passage width and a passage cross-sectional area, wherein at least one of: the cavity depth is greater than at least one of the passage length and the passage width, the passage length is greater than the passage width, and the cavity cross-sectional area is greater than the passage cross-sectional area.

The apparatus may include a pallet that supports a plurality of such wells. The passage of at least one of the wells may have a rim and the rim may have an adjacent trough.

For at least one of the wells, the passage length may be greater than the passage width and the direction of the passage length may be aligned to reduce at least one of the probability, magnitude and rate of spillage of material in comparison to the passage length being equal to the passage width. In this regard, reduce includes reducing spillage of material toward an adjacent one of the wells, which might be accomplished by configuring the direction of the passage length to not intersect another one of the wells.

The apparatus might further include a first abutment and a second abutment connected to support opposite ends of the pallet, and a base connected to anchor the first abutment and the second abutment. The base might have a lip. The base, the first abutment, the second abutment and the pallet might form a housing and define between them a compartment beneath the wells. This housing might be formed from injection molded thin plastic that can be sterilized using gamma radiation or an electron beam, for example, and packaged individually for disposable single usage.

The housing might include at least one divider extending from the base toward the pallet to divide the compartment into sub-compartments, wherein the number of sub-compartments might equal the number of wells.

The apparatus might further include a frame having: a first leg and a second leg, and a deck extending between the first leg and the second leg and having a receptacle to receive and support the housing. In this regard, the first leg, the second leg and the deck may substantially form a sheet, and the receptacle might pass through the deck and have an interior flange to engage a perimeter of the pallet and support the housing. At least one of the first abutment and the second abutment might have a stop that cooperates with the receptacle to retain the housing within the receptacle.

At least one of the first leg and the second leg may include a handle portion, perhaps curved. The frame may also include an aperture aligned with the compartment, the aperture perhaps being tapered. In some embodiments, the aperture may be a plurality of apertures and there may be a plurality of dividers that extend from the base toward the pallet to divide the compartment into a plurality of sub-compartments equal to the plurality of apertures, and each of the apertures may be aligned with a respective one of the sub-compartments.

The frame 200 may be formed as an autoclavable metal, for example an aluminum extrusion or a stainless steel pressing or a disposable plastic, for example a black or otherwise opaque injection molded plastic. The frame 200 may thus resist penetration by light or actinic radiation and may be color-coded.

The apparatus may further include a lid having a closed position covering the receptacle and an open position exposing the receptacle. In this regard, the frame may have a track and the lid may have a runner complementary with the track, wherein the track and the runner cooperate to enable the lid to slide over the deck between its open position and its closed position. The deck may have a boss that urges against the lid to retain the lid in at least one of its open and its closed position. A center portion of the lid may be characterized on its underside by a recess, such that the boss does not urge against the centre portion of the lid, whereby the boss does not resist movement of the lid between its open position and its closed position. This recessed center portion may be formed by pressing out a knob.

The track might include at least one open end for mounting and removing the runner and the runner might include at least one cambered end.

The lid may resist transmission of at least one of visible light and actinic radiation, as may at least one of the housing and the frame. The lid may fit sufficiently tightly over the receptacle when in its closed position to resist evaporation of material in the well. The lid may be formed from a metal different than that of the frame, for example stainless steel. Alternatively, the lid may be formed from aluminum or opaque plastic.

According to another aspect of the present invention, there is provided an apparatus for holding material to be dispensed, comprising: a housing for holding the material and a frame having a substantially sheet-like form and having a receptacle that passes through the frame for receiving the housing.

Further aspects and advantages of the present invention will become apparent upon considering the following drawings, description, and claims.

DESCRIPTION OF THE INVENTION

The invention will be more fully illustrated by the following detailed description of non-limiting specific embodiments in conjunction with the accompanying drawing figures. In the figures, similar elements and/or features may have the same reference label. Further, various elements of the same type may be distinguished by following the reference label with a second label that distinguishes among the similar elements. If only the first reference label is identified in a particular passage of the detailed description, then that passage describes any one of the similar elements having the same first reference label irrespective of the second reference label.

1. BRIEF DESCRIPTION OF THE DRAWINGS

FIG. 1A is an exploded oblique top-left-front view of the apparatus of FIG. 1.

Figure 1:
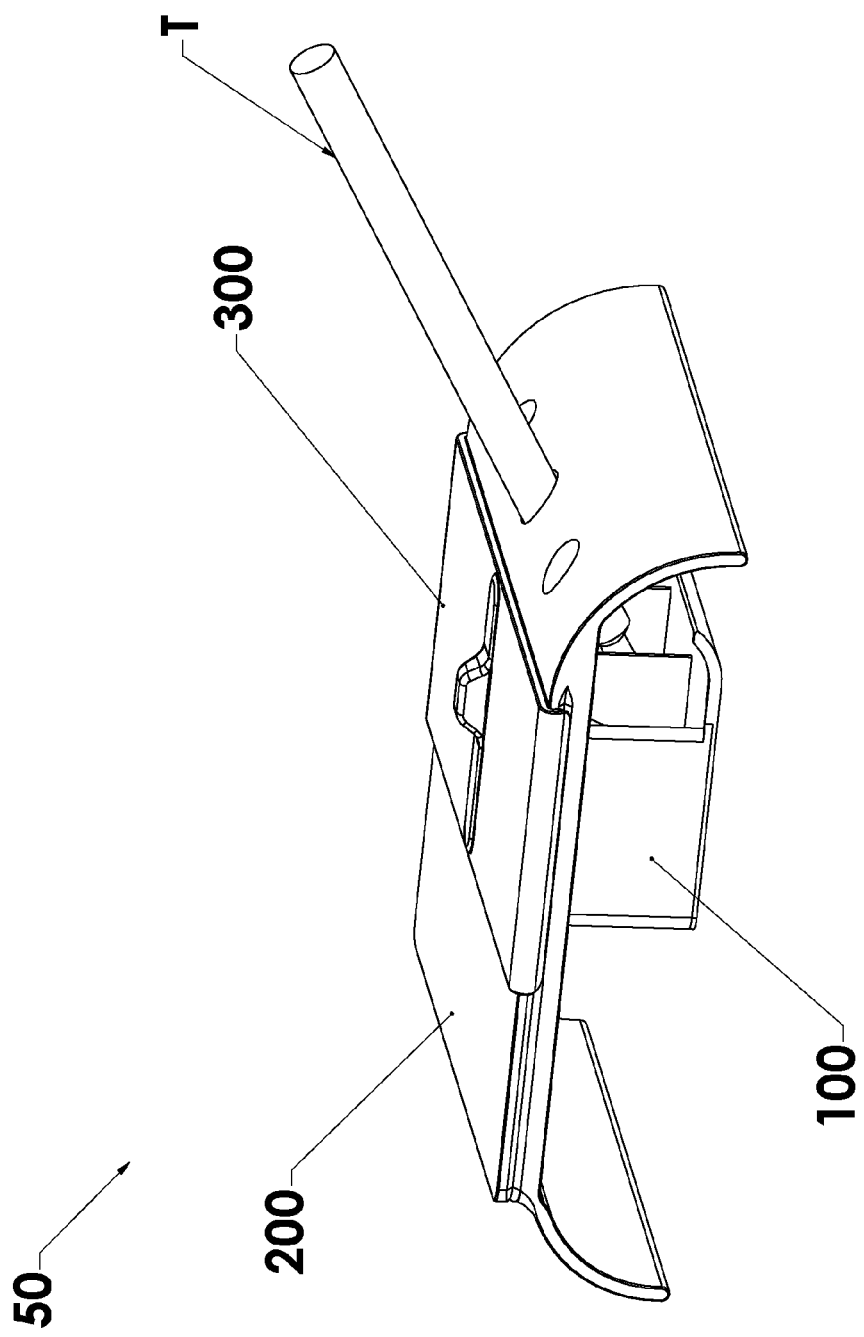
FIG. 1 is an oblique top-left-front view of an embodiment, in accordance of aspects of the present invention, of an apparatus for holding material to be dispensed, the apparatus having a housing, a frame and a lid.

2. DETAILED DESCRIPTION OF SPECIFIC EMBODIMENTS (a) Structure

The structure of the invention will now be illustrated by specific, non-limiting embodiments that exemplify aspects of the invention, which are shown in the drawing figures and described in greater detail herein.

| Table of Elements | |
|---|---|
| Name | Reference |
| Apparatus for holding material to be dispensed | 50 |
| Housing | 100 |
|   Pallet | 102 |
|     Well | 104 |
|       Cavity | 106 |
|       Passage | 108 |
|         Rim | 110 |
|         Trough | 112 |
|     Abutment | 114 |
|       Stop | 116 |
|     Base | 118 |
|       Lip | 120 |
|     Compartment | 122 |
|       Divider | 124 |
| Frame | 200 |
|   Deck | 202 |
|     Receptacle | 206 |
|       Flange | 208 |
|     Track | 210 |
|     Boss | 212 |
|   Leg | 204 |
|     Handle Portion | 214 |
|     Aperture | 216 |
| Lid | 300 |
|   Runner | 302 |
|   Knob | 304 |
|   Camber | 306 |
| Tool | T |

| Terminology | |
|---|---|
| Depth | Depth is a maximum linear distance of a thing measured between its top and its bottom in a direction that is vertical when the thing is in its normal rest position; the depth measured between the top and the bottom of a plane is 0. |
| Length | Length is a maximum linear distance of a thing measured perpendicularly to the direction of its depth. |
| Width | Width is a maximum linear distance of a thing measured perpendicularly to both the direction of its depth and the direction of its length and is less than or equal to its length. |
| Cross-sectional Area | Cross-sectional area is a maximum area of a thing measured in a plane parallel to both the direction of its length and the direction of its width. |
| Sheet | A sheet is a body that:<br>(a) is thin in comparison to its length and width at most locations;<br>(b) is substantially smooth or substantially continuous;<br>(c) may or may not be planar;<br>(d) may or may not be malleable, ductile, pliable, elastic; resilient, rigid or flexible; and<br>(e) may have voids. |

FIGS. 1 and 1A show an apparatus for holding material to be dispensed, according to one embodiment of the present invention, generally illustrated at 50.

The apparatus 50 may be formed as a housing 100 that may be supported within a frame 200 and may be covered by a lid 300. A tool T (not part of the invention), may be used to dispense the material, for example placing the material into the apparatus 50, mixing the material, and removing the material from the apparatus 50.

Figure 2:
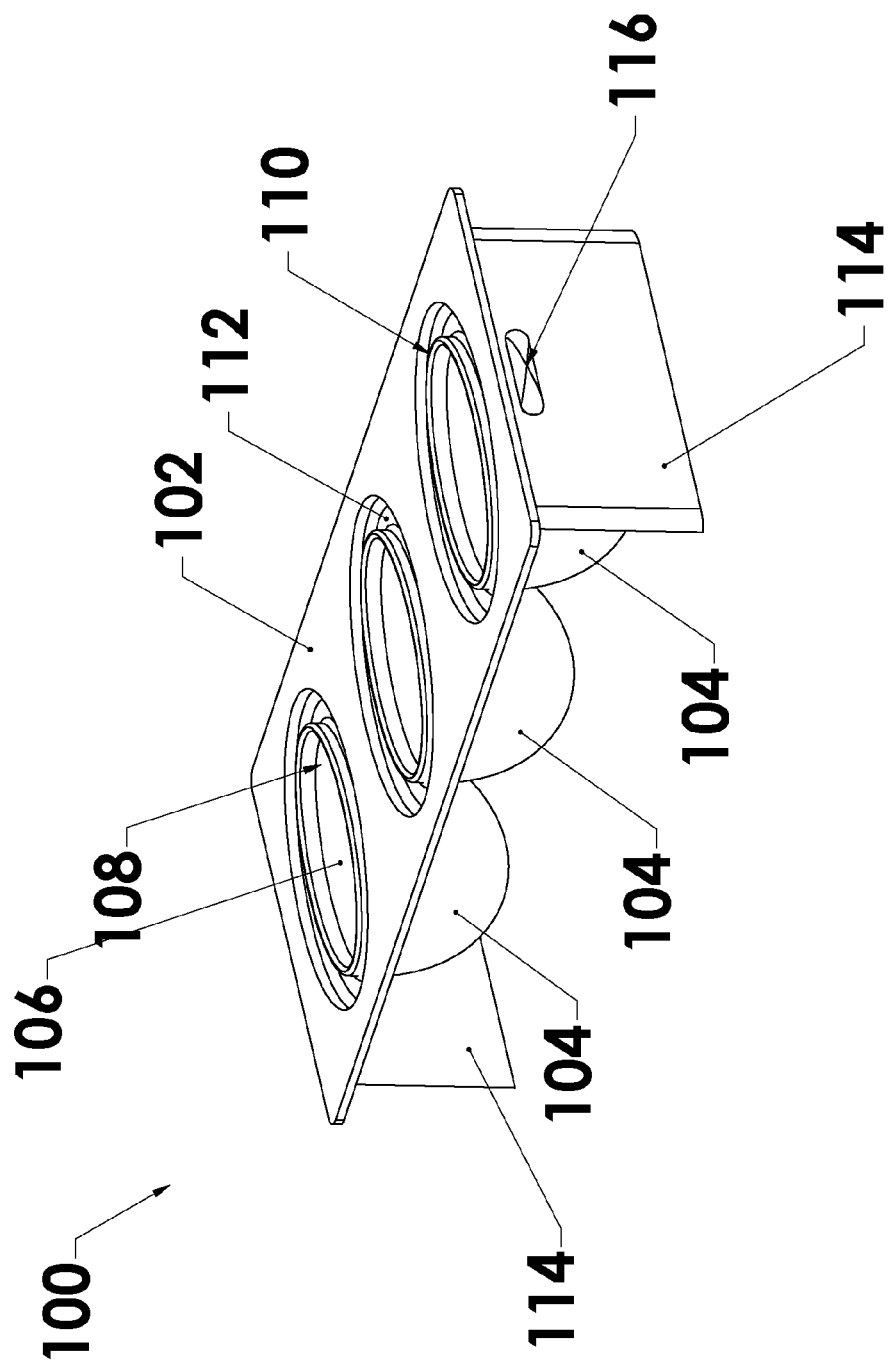
FIG. 2 is an oblique top-left-rear view of parts of the housing of FIG. 1.
Figure 3:
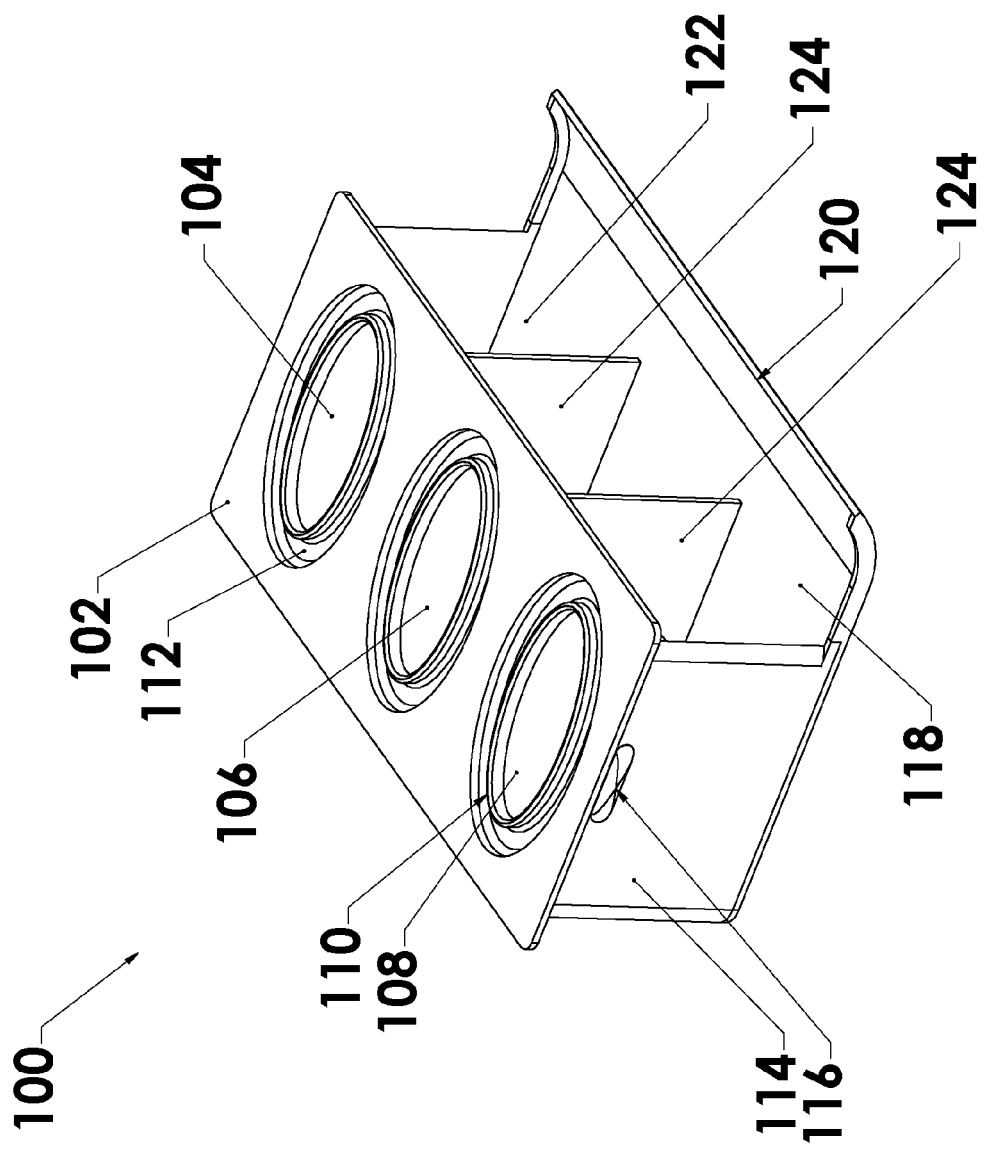
FIG. 3 is an oblique top-left-front view of the housing of FIG. 1.

Referring to FIGS. 2 and 3, it can be seen that at its simplest the housing 100, and more broadly the apparatus 50, is a well 104 having a cavity 106 for holding the material and a passage 108 in communication with the cavity, such that material can be placed into the cavity and removed from the cavity through the passage. The cavity 106 has a depth, a length, a width and a cross-sectional area. Similarly, the passage 108 has a depth, a length, a width and a cross-sectional area.

To resist premature setting of the material within the cavity 106 from exposure to the surrounding environment, the well 104 is configured to limit such exposure by limiting the proportion of material exposed. More specifically, the exposed cross-sectional area of the passage 108 is configured to be small in comparison to convention and to the volume of the cavity 106, which as illustrated may be ellipsoidal. This configuration may be accomplished, for example: by making the depth of the cavity 106 greater than at least one of the length of the passage 108 and the width of the passage 108, by making the length of the passage 108 greater than the width of the passage 108, or by making the cross-sectional area of the cavity 106 greater than the cross-sectional area of the passage 108.

A number of such wells 104 may be supported by a pallet 102, for example in a side-by-side arrangement. The passage 108 of at least one of the wells 104 may have a rim 110 to better contain the material in the cavity 106 from escaping, as illustrated the rim 110 having an inward cant for enhanced containment. To further resist material escaping, there may be a trough 112 adjacent the rim 110, for example fully circumscribing the rim 110 as illustrated; however, in some embodiments the rim 110 or the trough 112 may not be fully closed and may either inscribe or circumscribe the other.

It is desirable to configure wells 104 to resist spilling material, whether in general or into adjacent wells 104, causing cross-contamination. By configuring the length of a passage 108 to be greater than the width of the passage 108 one in effect forms a spout in the direction of the length of the passage 108 and discourages material from spilling in the direction of the width of the passage 108. In this regard, one can align the direction of the length of the passage 108 to reduce the probability, magnitude or rate of spillage of material in comparison to configurations in which the length of the passage 108 is equal to the width of the passage 108.

For example, by aligning the direction of the length of the passage 108 with an axis about which a well 104 is most likely to be tipped during use, spillage can be resisted.

As another example, the direction of the length of a passage 108 can be aligned to reduce spillage of material toward an adjacent well 104. This result might be accomplished by aligning the direction of the length of the passage 108 such that it does not intersect an adjacent well 104.

The housing 100 may further include a first abutment 114 and a second abutment 114 connected to support opposite ends of the pallet 102. At least one of the first abutment 114 and the second abutment 114 may include stop 116, which will be more fully described below with respect to the complementary frame 200. The stop 116 is illustrated as a positive protuberance, but those skilled in the art will recognize it might also be embodied otherwise, for example as a negative detent.

The housing 100 may further include a base 118 connected to anchor the first abutment 114 and the second abutment 114. The base 118 may include a containment lip 120, for example as illustrated providing both end and edge containment.

As illustrated, the base 118, the first abutment 114, the second abutment 114 and the pallet 102 define between them a compartment 122 beneath the plurality of wells 104. Additionally, there may be at least one divider 124 extending from the base 118 partially or fully toward the pallet 102 to divide the compartment 122 into a plurality of sub-compartments. The number of sub-compartments may conveniently be equal to the number wells 104 in some embodiments.

The housing 100 may be formed from injection molded thin plastic that can be sterilized using gamma radiation or an electron beam for example. Single housings 100 may be sterilely packaged for disposable single usage.

Figure 4:
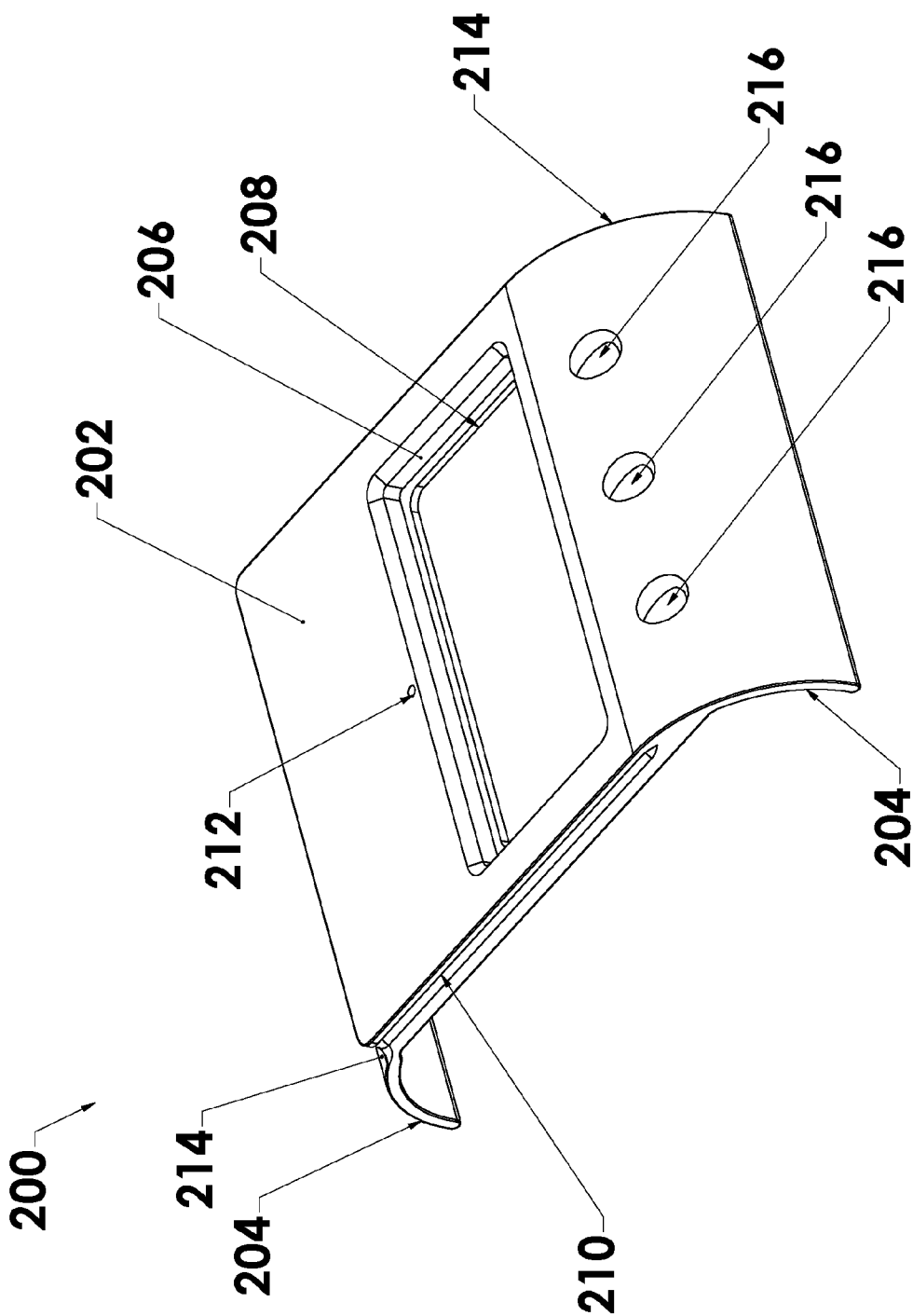
FIG. 4 is an oblique top-left-front view of the frame of FIG. 1.
Figure 5:
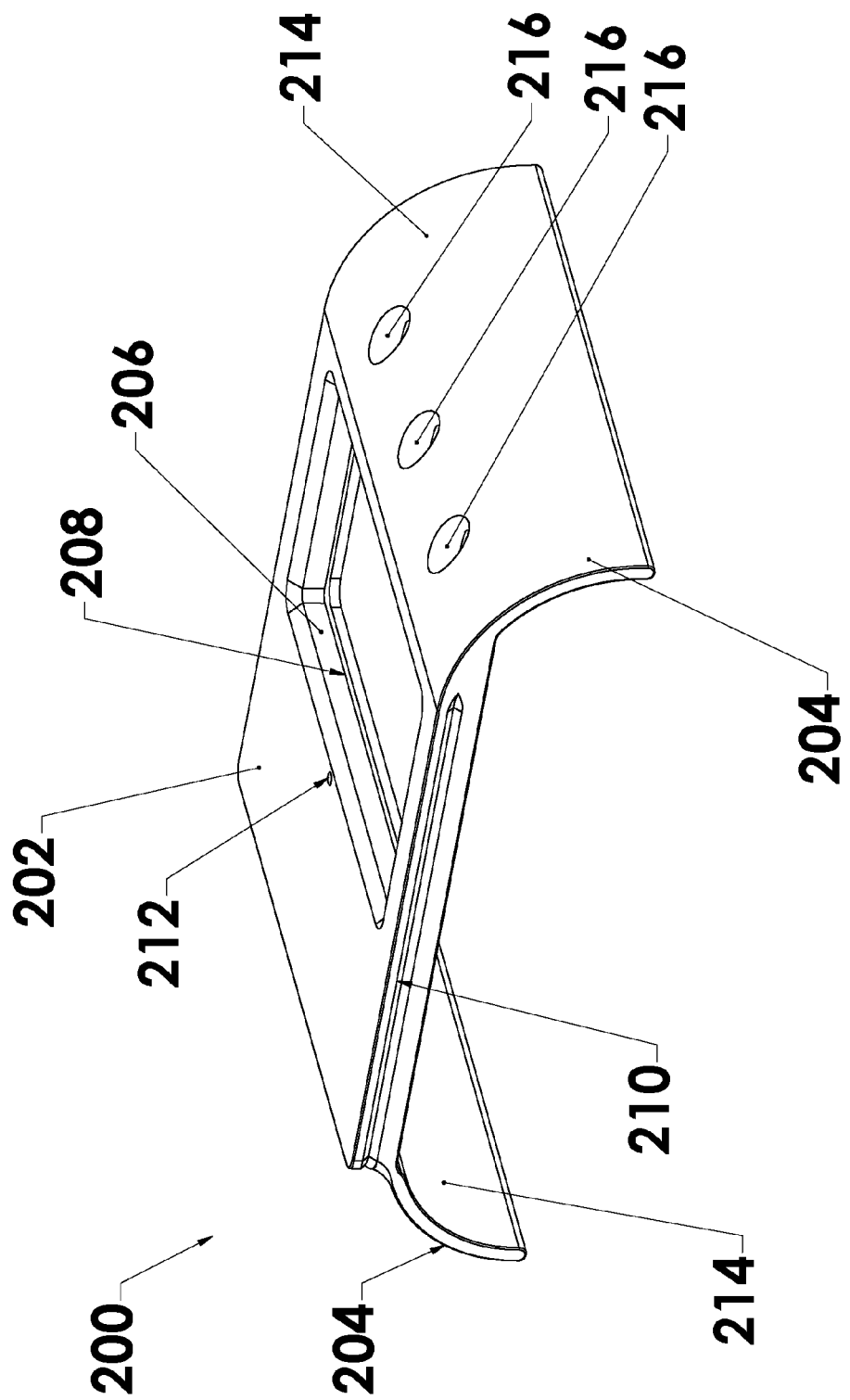
FIG. 5 is an oblique left-front view of the frame of FIG. 1.
Figure 6:
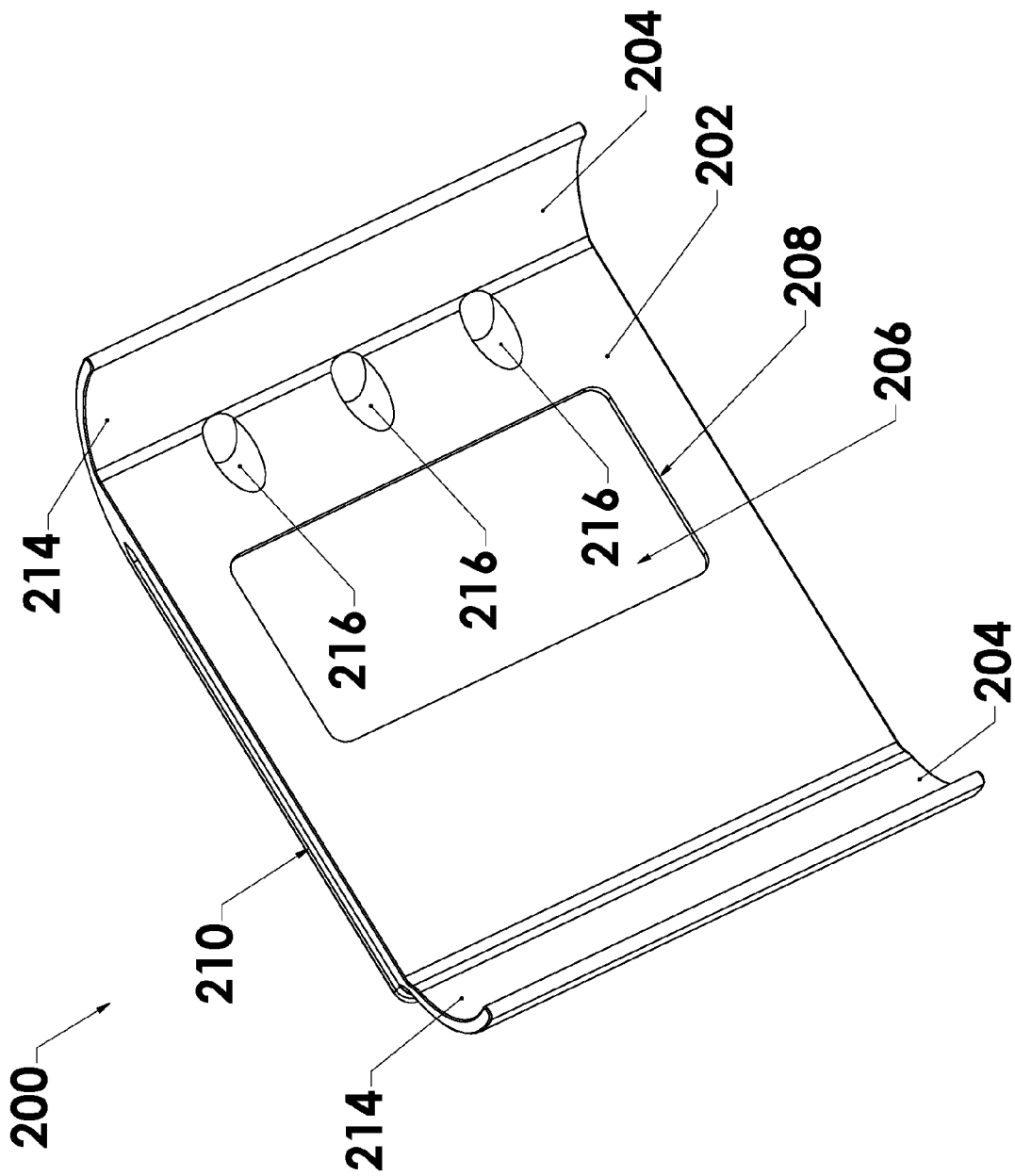
FIG. 6 is an oblique bottom-rear-left view of the frame of FIG. 1.

Referring to FIGS. 4-6, the frame 200 will now be described in greater detail. The frame 200 has a first leg 204 and a second leg 204, and a deck 202 extending between the first leg 204 and the second leg 204. As illustrated, the first leg 204, the second leg 204 and the deck 202 may substantially form a sheet, having an openness that is well adapted to cleaning and sterilization. In this regard, for safety the frame 200 can be formed from an autoclavable material, for example aluminum, for example as an extrusion. For safety and ease of use, the frame 200 can be color-coded to help a user quickly identify what material is being held in the apparatus 50.

The deck 202 has a receptacle 206 to receive and support the housing 100. As illustrated, the receptacle 206 passes through the deck 202, the receptacle 206 having an interior flange 208 to engage a perimeter of the pallet 102 and support the housing 100. As mentioned above, at least one of the first abutment 114 and the second abutment 114 has a stop 116 that cooperates with the receptacle 206 to retain the housing 100 within the receptacle 206, in this embodiment as a press-fit.

At least one of the first leg 204 and the second leg 204 has a portion configured as a handle portion 214, to provide a place for a user to comfortably and securely hold the apparatus 50 for precise use. As illustrated, the handle portion 214 is curved and without sharp corners that might cut a user's hand or glove or might trap contaminants.

The frame 200 further includes at least one aperture 216 passing through either the deck or, as illustrated, one of the legs 204. The aperture 216 is adapted to receive and retain the tool T (not part of the invention). In this regard, the aperture 216 may be tapered with a larger outward facing end to receive the tool T and a smaller inwardly facing end to retain the tool T The aperture 216 may be aligned with the compartment 122 when the housing 100 is in the receptacle 206, such that a tip of the tool T inserted into the aperture is received within the compartment 122, without significant bending stresses on the tip. In some embodiments, the compartment 122 may be fully or partially closed opposite the aperture 216.

In some embodiments, there may be a number of apertures 216 and the compartment 122 may be divided by dividers 124 into that same number of sub-compartments, such that each of the number of apertures 216 is aligned with a respective one of the number of sub-compartments. In this way, a number of tools T (not part of the invention) can be protected from cross-contamination within respective sub-compartments. Conveniently, this number of apertures 216 and sub-compartments may be equal to the number of wells 104.

The frame further includes a track 210, embodiment for example as a lateral groove cut into one side or both sides of the deck 202 and extending between the first leg 204 and the second leg 204, here shown as being open at one end and closed at the opposite end. The track 210 will be more fully described below with respect to the complementary lid 300. Those skilled in the art will recognize that the track 210 may be embodied as a positive spline instead of a negative groove and that one or both ends may be open or closed.

The frame further includes a boss 212 on the surface of the deck 202 adjacent the receptacle 206. The boss 212 will be more fully described below with respect to the complementary lid 300.

Figure 7:
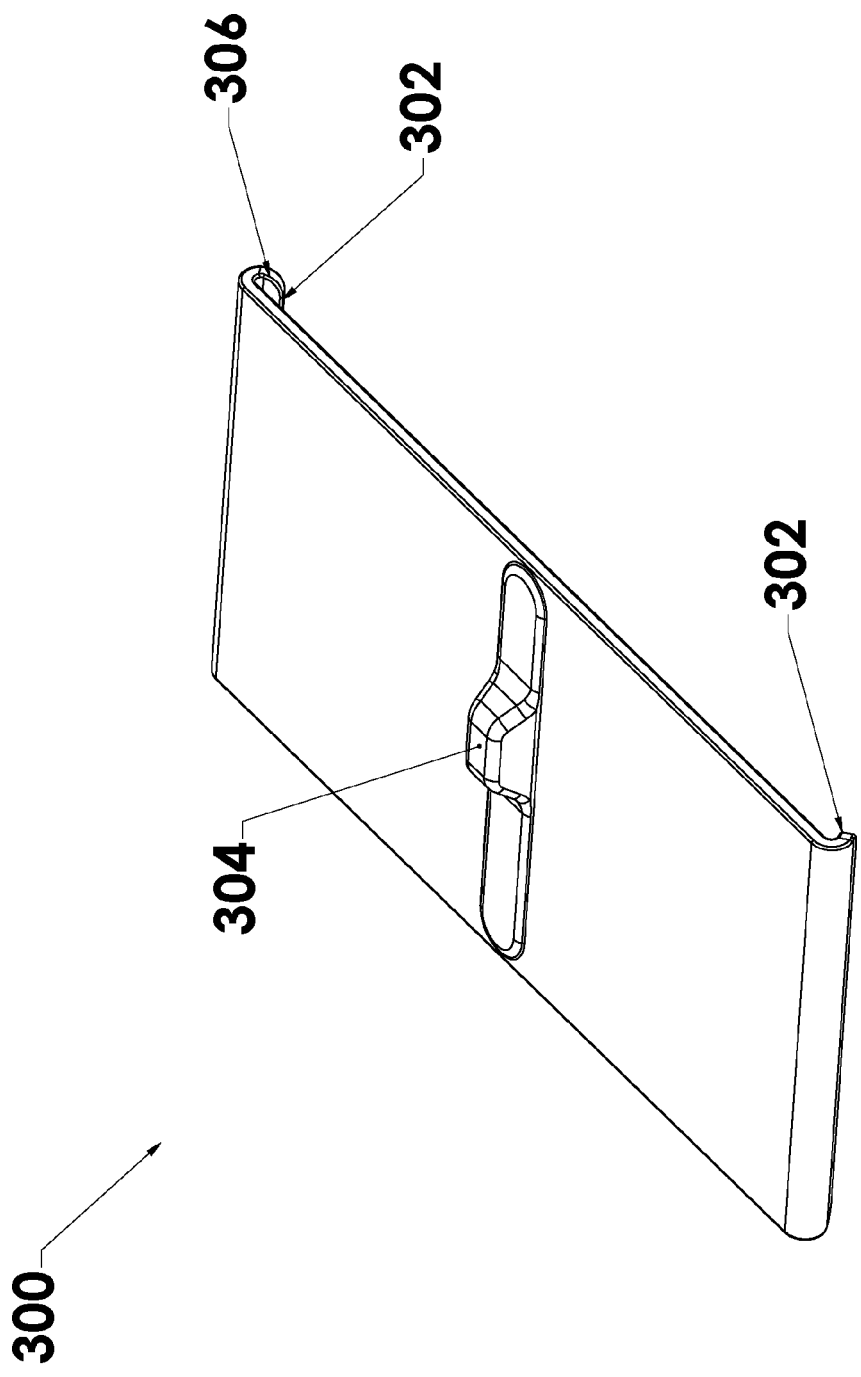
FIG. 7 is an oblique top-left-front view of the lid of FIG. 1.
Figure 8:
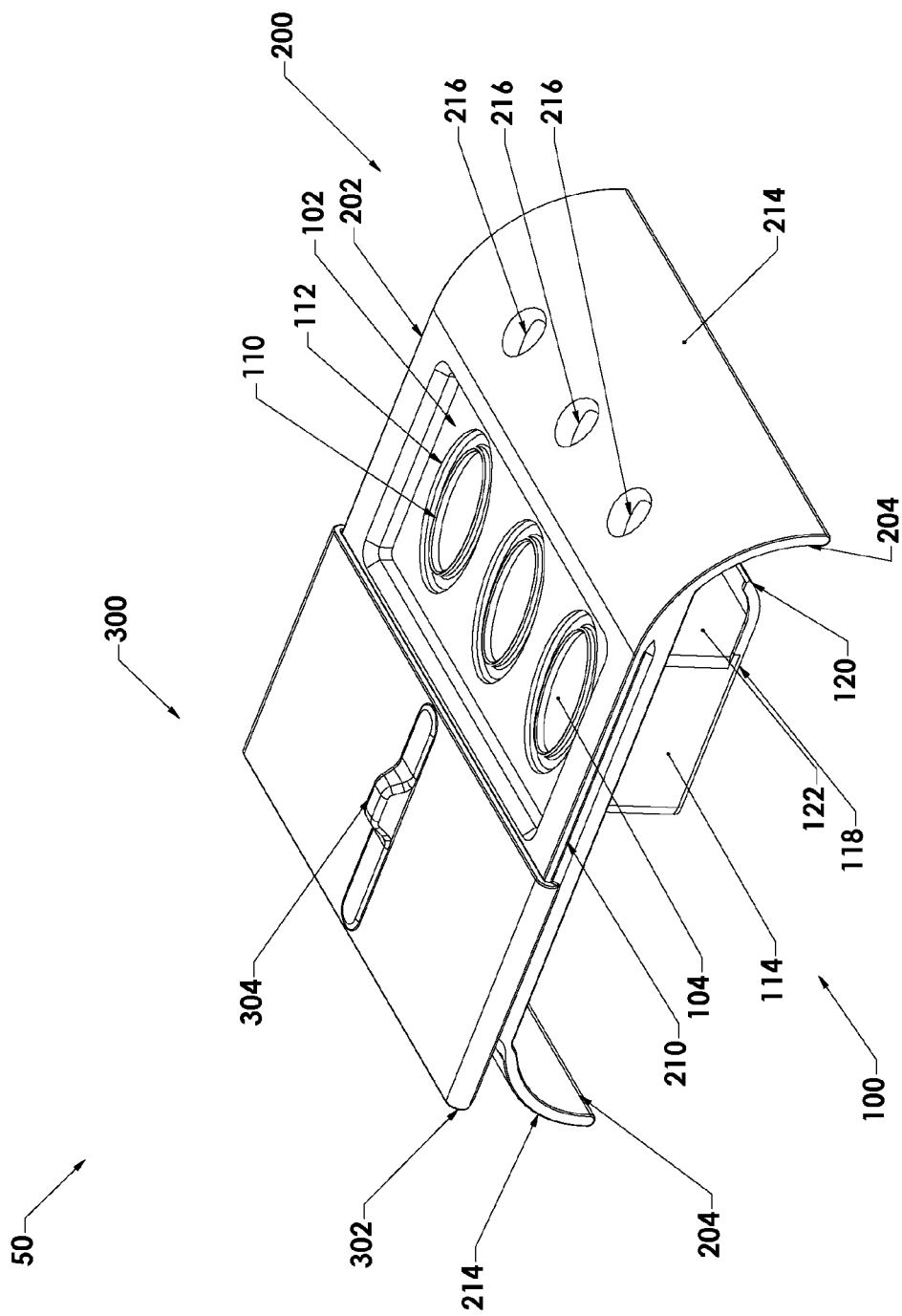
FIG. 8 is an oblique top-left-front view of the apparatus of FIG. 1, with the lid in its open position.
Figure 9:
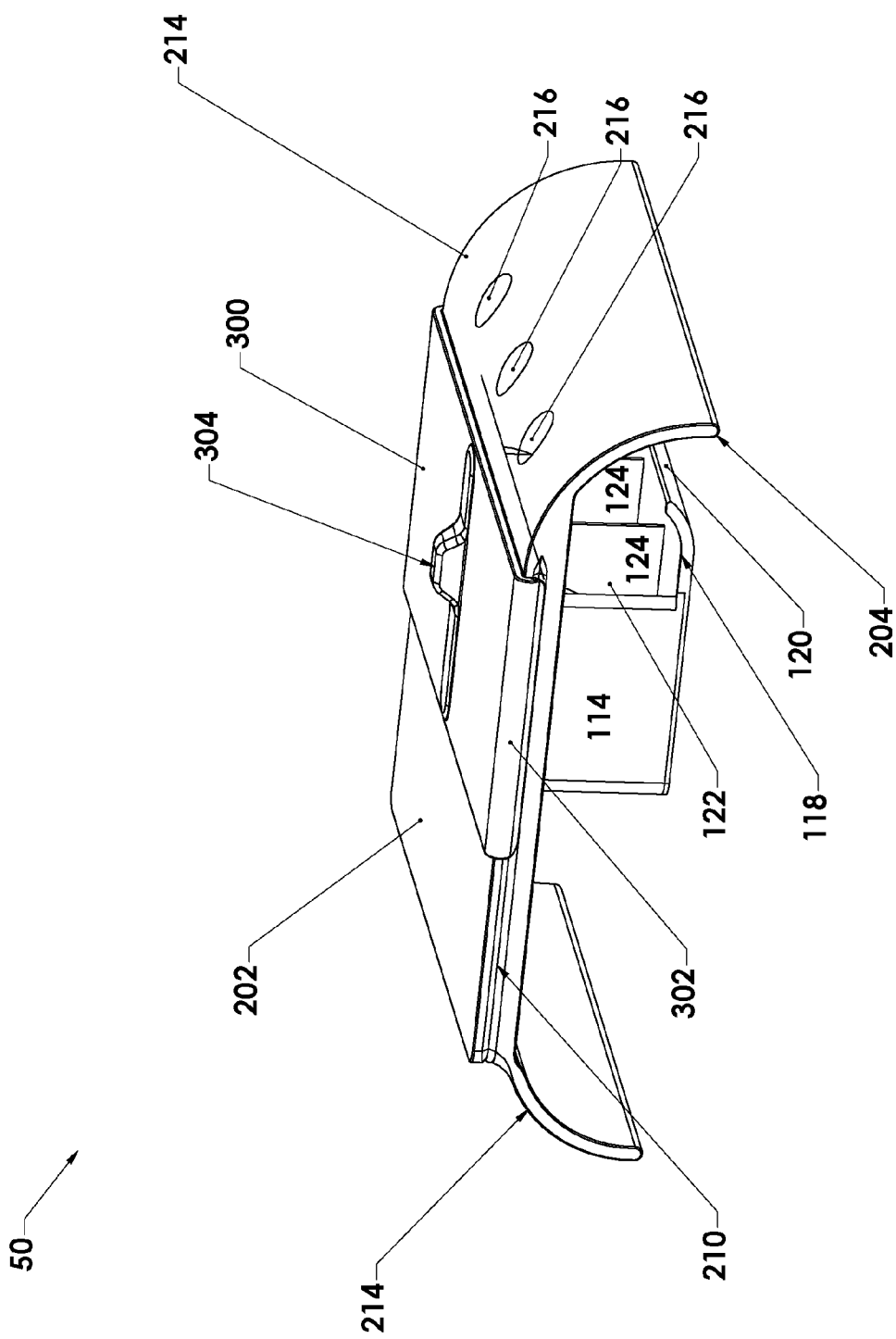
FIG. 9 is an oblique top-left-front view of the apparatus of FIG. 1, with the lid in its closed position.

Referring to FIGS. 7-9, the lid 300 will now be described in further detail. The lid 300 is sized and shaped to cover the receptacle 206 and hence the wells 104 when the housing 100 is retained within the receptacle 206. The lid 300 is configured to move between a closed position, so covering the receptacle 206, and an open position in which the receptacle 206 and the wells 104 are exposed for access by a user.

As illustrated, the lid 300 has at least one runner 302 that is complementary with the track 210 on the frame 200, the track 210 and the runner 302 cooperating to enable the lid 300 to slide over the deck 202 between its open position and its closed position. A knob 304, as illustrated on the top of the lid 300, provides a helpful grip for urging the lid 300 between its open and closed position.

The boss 212 on the deck 202 urges against the lid 300 to retain the lid 300 in either its open or its closed position. In this regard, a centre portion of the lid 300 may be characterized on its underside by recess, such that the boss 212 can urge against only the edges of lid 300 and does not urge against the centre portion of the lid 300, whereby the boss 212 retains the lid 300 in either its open or its closed position but does not resist the movement of the lid 300 between its open position and its closed position. This recessing might be embodied, for example as illustrated, by pressing out the knob 304 from the lid 300 during manufacture, such that the underside of the knob 304 is hollow and the topside of the lid 300 is characterized by the knob 304.

As illustrated, the open end of the track 210 enables the runner 302 and hence the lid 300 to be mounted on and removed from the frame 200. Each end of the runner 302 may include a camber 306 that both facilitates engagement of the runner 302 with the track 210 and also resists cutting the hand or the glove of a user.

The lid 300, and more generally the housing 100, the frame 200 and the apparatus 50, resists transmission of at least one of visible light and actinic radiation. In this regard, the lid 300 may be formed from metal, for example by sheet-forming or extruding, or from opaque plastic, for example by injection molding. The lid 300 may also fit sufficiently tightly over the receptacle 206, when in its closed position, as to resist evaporation of material in the well 104. By making the lid 300 from a metal other than that of the frame 200, for example stainless steel or plastic, one can reduce wear between the track 210 and the runner 302.

(b) Operation

With reference now to FIGS. 1-9, typical operation of these embodiments of an apparatus for holding material to be dispensed 50 will now be described.

A user working in a sterile environment, for example a medical or dental surgery, would remove a disposable sterile housing 100 from its individual sterile packaging. He would select an autoclaved frame 200, perhaps color-coded to identify the material to be held for dispensing. He would insert the housing 100 into the receptacle 206 in the frame, such that the pallet 102 of the housing abuts the flange 208 in the receptacle 206. The stop 116 on at least one of the abutments 114 of the housing 100 would urge against the receptacle 206 to further retain the housing 100 within the receptacle 206.

For each desired respective well 104 in the housing 100, the user would place material into the cavity 106 through the passage 108, while either resting the frame 200 on a surface such as a table or holding the frame 200 conveniently in hand, for example by the handle portion 214 of the first or second leg 204. The user might use an autoclaved tool T (not part of the invention) to place and mix material within the cavity 106 and later to remove it for dispensing through the passage 108.

The rim 110 and the trough 112 of the well 104 reduce spillage of the material from the well 104, including spillage into an adjacent well 104. The user can further resist spillage from the well 104 by holding the frame 200 oriented so as to align the direction of the length of the passage 108 with an axis about which the well 104 is most likely to be tipped during use.

Continuing with preparation, the user would install the lid 300 on the frame 200, if it was not already installed, by engaging the runner 302 with the track 210, the camber 306 on the runner 302 easing such engagement. The user would then draw on the knob 304 to place the lid 300 into its closed position over the receptacle 206 in the frame 200, thereby covering the one or more wells 104 underneath and protecting the held material from spillage, evaporation or premature setting through exposure to visible light or actinic radiation, for example, or in general loss or contamination. The boss 212 on the deck 202 of the frame 200 would urge against the lid 300 to hold the lid 300 in its closed position.

To finish preparation, the user would optionally insert for convenient storage one or more tools T (not part of the invention) through respective one or more apertures 216 in the frame 200, the respective tips of the respective tools T resting in the compartment 122 in the housing, desirably divided with dividers 124 into a like number of respective sub-compartments to resist cross-contamination. The lip 120 of the base 118 resists spillage from the compartment 122 of any residue flowing from the tools T.

For use, the user would similarly place the apparatus 50 on a convenient nearby surface such as a table or operating tray or would hold the handle portion 214. He would then draw on the knob 304, for example with the thumb of his hand that is holding the handle portion 214, to alternately move the lid 300 between its closed and open position as needed to alternately dispense material and protect the material held in the wells 104.

To dispense material, the user would remove a tool T from an aperture 216 in the frame 200 and insert the tool T into the cavity 106 of the well 104 holding material to be dispensed, through the passage 108. Once finished dispensing the material, the user would close the lid 300 and insert the tool T back through the aperture 216 into the compartment 122.

When finished, the user would remove all tools T from the compartment 122 and the apertures 216 and remove the lid 300 from the frame 200. The user would remove the housing 100 from the frame 200 and safely dispose of the single usage housing 100. The user would then autoclave the frame 200, the lid 300 and the tools T, if not made of single usage, disposable material, such as plastic.

(c) Description Summary

Thus, it will be seen from the foregoing embodiments and examples that there has been described an apparatus for holding material to be dispensed in a surgical setting, and in particular that:

allows for small portions of material to be dispensed efficiently resisting cross-contamination, resists evaporation of volatile agents in the material being dispensed, reduces exposure of the material to light and actinic radiation during intermittent use, and supports autoclaving in order to fulfill sterilization and infection control standards in surgical setting.

While specific embodiments of the invention have been described and illustrated, such embodiments should be considered illustrative of the invention only and not as limiting the invention as construed in accordance with the accompanying claims.

It will be understood by those skilled in the art that various changes, modifications and substitutions can be made to the foregoing embodiments without departing from the principle and scope of the invention expressed in the claims made herein. For example parts may be formed from substances other than the examples provided. Similarly, parts may be made either disposable for single usage or else sterilizable for multiple usage in combinations other than as illustrated. In selecting a substance that will be sterilized using a process other than heating (autoclaving), for example because the substance cannot suitably withstand the necessary heat, one should select a substance that has the necessary chemical resistance and radiation resistance to the sterilization process so that the substance will not subsequently contaminate material it contacts and so that parts made from the substance will not break prematurely. For example, if using a sterilization process that includes gamma radiation, an electron beam or the like, one might select polyethylene as a substance.

While the invention has been described as having particular application for surgery, those skilled in the art will recognize it has wider application, for example dentistry and medical or other industries where materials are dispensed and used in small amounts and sterilization techniques are or should be exercised.

What is claimed is:

1. An apparatus for holding material to be dispensed, comprising:
   a) a plurality of wells having:
      i) a cavity for holding the material, the cavity having a cavity depth, a cavity length, a cavity width and a cavity cross-sectional area and,
      ii) a passage in communication with the cavity, such that material can be placed into the cavity and removed from the cavity through the passage, the passage having a passage depth, a passage length, a passage width and a passage cross-sectional area, wherein at least one of:
         A) the cavity depth is greater than at least one of the passage length and the passage width,
         B) the passage length is greater than the passage width, and
         C) the cavity cross-sectional area is greater than the passage cross-sectional area,
   b) a pallet that supports the plurality of wells,
   c) a first abutment and a second abutment connected to support opposite ends of the pallet,
   d) a base connected to anchor the first abutment and the second abutment, wherein the base, the first abutment, the second abutment and the pallet form a housing and define between them a compartment beneath the plurality of wells, and
   e) a frame having:
      i) a first leg and a second leg, and
      ii) a deck extending between the first leg and the second leg and having a receptacle to receive and support the housing,
      wherein the first leg, the second leg and the deck substantially form a sheet, and
      wherein the receptacle passes through the deck, the receptacle having an interior flange to engage a perimeter of the pallet and support the housing.

2. An apparatus as claimed in claim 1, wherein at least one of the first abutment and the second abutment has a stop that cooperates with the receptacle to retain the housing within the receptacle.

3. An apparatus as claimed in claim 1, wherein at least one of the first leg and the second leg includes a handle portion.

4. An apparatus as claimed in claim 3, wherein the handle portion is curved.

5. An apparatus as claimed in claim 1, wherein the frame further includes an aperture aligned with the compartment.

6. An apparatus as claimed in claim 5, wherein the aperture is tapered.

7. An apparatus as claimed in claim 5, wherein:
   a) the aperture is a plurality of apertures,
   b) a plurality of dividers extend from the base toward the pallet to divide the compartment into a plurality of sub-compartments equal to the plurality of apertures, and
   c) each of the plurality of apertures is aligned with a respective one of the plurality of sub-compartments.

8. An apparatus as claimed in claim 1, wherein the frame is an autoclavable aluminum extrusion.

9. An apparatus as claimed in claim 8, wherein the frame is color-coded.

10. An apparatus as claimed in claim 1, further including a lid having a closed position covering the receptacle and an open position exposing the receptacle.

11. An apparatus as claimed in claim 10, wherein:
    a) the frame has a track, and
    b) the lid has a runner complementary with the track, wherein the track and the runner cooperate to enable the lid to slide over the deck between its open position and its closed position.

12. An apparatus as claimed in claim 11, wherein the deck has a boss that urges against the lid to retain the lid in at least one of its open and its closed position.

13. An apparatus as claimed in claim 12, wherein a center portion of the lid is characterized on its underside by a recess, such that the boss does not urge against the centre portion of the lid, whereby the boss does not resist movement of the lid between its open position and its closed position.

14. An apparatus as claimed in claim 13, wherein the recessed center portion is formed by pressing out a knob.

15. An apparatus as claimed in claim 11, wherein the track includes at least one open end for mounting and removing the runner.

16. An apparatus as claimed in claim 15, wherein the runner includes at least one cambered end.

17. An apparatus as claimed in claim 10, wherein the lid resists transmission of at least one of visible light and actinic radiation.

18. An apparatus as claimed in claim 17, wherein at least one of the housing and the frame resists transmission of at least one of visible light and actinic radiation.

19. An apparatus as claimed in claim 10, wherein the lid fits sufficiently tightly over the receptacle when in its closed position to resist evaporation of material in the well.

20. An apparatus as claimed in claim 10, wherein the lid is formed from a metal different than that of the frame.

21. An apparatus as claimed in claim 20, wherein the lid is formed from at least one of stainless steel and opaque plastic.

\* \* \* \* \*